(12) United States Patent
Sund et al.

(10) Patent No.: US 11,534,326 B2
(45) Date of Patent: Dec. 27, 2022

(54) BODY SIDE MEMBER OF AN OSTOMY APPLIANCE

(71) Applicant: Coloplast A/S, Humlebaek (DK)

(72) Inventors: Anders Grove Sund, Alleroed (DK); Lars Stendevad Windeballe, Virum (DK); Kasper Friis, Alleroed (DK); Anders Ravn Joergensen, Copenhagen (DK); Jais Ask Hansen, Jaegerspris (DK)

(73) Assignee: Coloplast A/S, Humlebaek (DK)

( * ) Notice: Subject to any disclaimer, the term of this patent is extended or adjusted under 35 U.S.C. 154(b) by 443 days.

(21) Appl. No.: 16/498,402

(22) PCT Filed: Apr. 9, 2018

(86) PCT No.: PCT/DK2018/050071
§ 371 (c)(1),
(2) Date: Sep. 27, 2019

(87) PCT Pub. No.: WO2018/188708
PCT Pub. Date: Oct. 18, 2018

(65) Prior Publication Data
US 2020/0046541 A1    Feb. 13, 2020

(30) Foreign Application Priority Data
Apr. 10, 2017   (DK) .......................... PA 2017 70257

(51) Int. Cl.
*A61F 5/443*    (2006.01)
*A61F 5/448*    (2006.01)
*A61F 5/44*     (2006.01)

(52) U.S. Cl.
CPC ............ *A61F 5/443* (2013.01); *A61F 5/4404* (2013.01); *A61F 5/448* (2013.01)

(58) Field of Classification Search
CPC combination set(s) only.
See application file for complete search history.

(56) References Cited

U.S. PATENT DOCUMENTS

| 3,081,771 A | * | 3/1963 | Lee | A61F 5/443 |
| | | | | 604/344 |
| 4,753,703 A | * | 6/1988 | Jensen | A61F 5/443 |
| | | | | 414/791.2 |
| 4,793,337 A | * | 12/1988 | Freeman | A61L 15/58 |
| | | | | 442/151 |

(Continued)

FOREIGN PATENT DOCUMENTS

| GB | 1256866 A | * | 12/1971 | ............ A61F 5/443 |
| GB | 1256866 A | | 12/1971 | |

(Continued)

*Primary Examiner* — Guy K Townsend
(74) *Attorney, Agent, or Firm* — Coloplast Corp., Coloplast A/S; Nick Baumann (57) ABSTRACT

A body side member of an ostomy appliance comprising releasable material provided in one or more overlays covered by individual cover layers. The releasable material is adapted to engage with stomal output to prevent breakdown of the adhesive attaching the ostomy appliance to the skin surface around a stoma of a user. The cover layers are individually removable and can be removed one at a time to release the releasable material.

21 Claims, 4 Drawing Sheets

(56) References Cited

U.S. PATENT DOCUMENTS

| | | | |
|---|---|---|---|
| 5,051,259 A * | 9/1991 | Olsen | A61F 13/0213 428/355 R |
| 5,074,852 A * | 12/1991 | Castellana | A61F 5/443 604/336 |
| 5,591,820 A * | 1/1997 | Kydonieus | C08G 18/73 528/905 |
| 5,714,543 A * | 2/1998 | Shah | C08L 29/00 525/123 |
| 5,912,059 A * | 6/1999 | Jones | A61F 5/443 428/35.5 |
| 6,764,474 B2 | 7/2004 | Nielsen et al. | |
| 6,869,422 B2 * | 3/2005 | Fenton | A61F 5/445 604/338 |
| 7,347,844 B2 * | 3/2008 | Cline | A61F 5/448 604/338 |
| 7,857,796 B2 * | 12/2010 | Cline | A61F 5/448 604/277 |
| 8,439,883 B1 * | 5/2013 | Johnsen | A61F 5/448 604/338 |
| 2002/0088080 A1 * | 7/2002 | Fenton | A61F 5/445 604/338 |
| 2004/0193122 A1 * | 9/2004 | Cline | A61F 5/448 604/332 |
| 2004/0223944 A1 * | 11/2004 | Capelli | A61K 47/585 424/618 |
| 2004/0230170 A1 * | 11/2004 | Fenton | A61F 5/445 604/336 |
| 2006/0141016 A1 * | 6/2006 | Sambasivam | A61P 17/00 424/773 |
| 2008/0119804 A1 * | 5/2008 | Cline | A61F 5/445 604/338 |
| 2008/0319368 A1 * | 12/2008 | Lykke | A61F 13/025 602/57 |
| 2009/0311307 A1 * | 12/2009 | Lykke | B05D 3/00 424/443 |
| 2010/0168693 A1 * | 7/2010 | Edvardsen | A61F 5/451 604/355 |
| 2011/0213322 A1 * | 9/2011 | Cramer | A61F 5/443 604/332 |
| 2013/0123678 A1 * | 5/2013 | Carty | A61F 13/0253 602/54 |
| 2015/0284597 A1 * | 10/2015 | Carty | C09J 7/38 206/229 |
| 2015/0359656 A1 * | 12/2015 | Hansen | A61F 5/445 604/344 |
| 2016/0235582 A1 * | 8/2016 | Moavenian | A61F 5/448 |
| 2016/0302959 A1 * | 10/2016 | Kavanagh | A61F 5/443 |
| 2017/0095431 A1 * | 4/2017 | Andrews | A61K 9/7007 |

FOREIGN PATENT DOCUMENTS

| | | | |
|---|---|---|---|
| GB | 2322302 A * | 8/1998 | A61F 5/443 |
| GB | 2322302 A | 8/1998 | |
| RU | 2553934 C2 | 6/2015 | |
| RU | 2575907 C2 | 2/2016 | |
| RU | 2582426 C2 | 4/2016 | |
| WO | 2017190752 A1 | 11/2017 | |

* cited by examiner

BODY SIDE MEMBER OF AN OSTOMY APPLIANCE

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and for these ostomists in particular safe, reliable and efficient ostomy devices are highly desirable. Numerous attempts have been made to provide ostomy devices to meet such requirements, e.g. the requirement of prolonged wear time, but the provision of sufficient efficiency to achieve a satisfactory long wear time of ostomy devices continues to be an unmet need.

Ostomists and health care professionals alike would welcome improvements in ostomy devices to better meet such requirements.

SUMMARY

The present disclosure provides aspects of a body side member of an ostomy appliance according to the appended claims. The disclosure further provides an ostomy appliance including a body side member as disclosed herein.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate" moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to a proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

Moreover, "releasable material" should be interpreted to include moldable and squeezable materials as well as including permanently deformable and shape-memory materials (i.e. materials capable of recovering to their original shape after a deformation). Also, in some implementations, the releasable material may be non-deformable itself (i.e. no significant deformation of the dimensions of a mass or volume "per volume unit" of the material is possible). However, it may be possible to manipulate the material in the sense of moving it in relation to other components. Additionally, or alternatively, "releasable" should be interpreted to relate to any materials that can be moved and/or manipulated by the hands or fingers of an average person without using significant force. In embodiments, the releasable material is a sacrificial component of the body side member, i.e. a material suitable for being "sacrificed" to avoid or slow the breaking down of the adhesive of the body side member and/or any of the other components of the body side member. In some implementations, the releasable material includes a matrix of material from which matrix one or more active components of the releasable material is configured to be released. In other implementations, an entirety of the releasable material is configured to be released from its respective overlay.

By stomal output is herein meant the solid and/or liquid effluents from a stoma, being faeces and/or urine in substantially solid and/or a more or less viscous form and/or mucins secreted from the epithelial layer of the alimentary canal. In the case of a colostomy (large intestine), the output can be quite solid, whereas an ileostomy (small intestine) produces more liquid or fluid-like output. The output may contain digestive juices including enzymes and other components that can be aggressive to the skin and can cause maceration of the skin surface upon contact therewith, as well as comprising other components that can attack and degrade the adhesive securing the ostomy appliance to the user's skin.

The use of the phrase "substantially" as a qualifier of certain features or effects throughout this disclosure, is intended to simply mean that any deviations are within tolerances that would normally be expected by the skilled person in the relevant field.

In one aspect, the present disclosure relates to a body side member of an ostomy appliance comprising a backing layer comprising a proximal surface and a distal surface. At least a portion of the proximal surface of the backing layer comprises an adhesive. The body side member comprises a centre portion. At least the centre portion is prepared for the provision of a stoma receiving opening extending through the body side member. The body side member further includes one or more overlays of a releasable material of which at least one is provided on a portion of the distal surface of the backing layer. In this disclosure, "overlay" should be understood strictly in relation to the releasable material meaning that an "overlay" is not intended to be understood in a broad sense as any kind of material or component on top (wholly or partially) of another material or component. Each of the one or more overlays of releasable material is covered by an individual cover layer. In this disclosure, "individual" should be understood as meaning "separate" (or distinct from other cover layers). Each individual cover layer is configured to be individually removable from off a respective overlay of releasable material. When a cover layer is removed from off a respective overlay of releasable material, a surface of the respective (that particular) overlay is exposed similar as with respect to the use of the wording "overlay", also in regard to the wording "cover" or "cover layer", the "cover layer" wording in intended to be understood as concerning a covering ("screening" or "cloaking") in relation to the releasable material meaning that "cover layer" is not intended to be understood in a broad sense as any kind of component overlapping (wholly or partially) another component for any kind of reason. In other words, each individual cover layer covers one overlay of releasable material. Each individual cover layer can be individually removed, i.e. removed one at a time to uncover or bring out one overlay of releasable material at a time. When a surface of the overlay of releasable material becomes exposed, the releasable material can engage with or take up moisture from stomal output, and/or moisture emanating from the mucous membrane of the stoma and/or from the skin surface of the user.

When a body side member of an ostomy appliance is applied to the skin surrounding a stoma, an adhesive provides a tight fit to the skin, to avoid the output from proceeding down under the wafer and damage the skin and degrade the adhesive on the proximal surface. Such stomal output "creeping under" the body side member is to be avoided as much as possible as it may lead to maceration of the skin and degradation of the adhesive resulting in leakage and unintended detachment of the body side member.

In embodiments, the releasable material can begin to release one or more substances suitable for blending in with the stomal output and/or moisture when the releasable material is engaged by the output or moisture. In embodiments, such one or more substances can include or provides a sacrificial material. In this context, sacrificial should be interpreted as a material that is sacrificed to the aggressive stomal output, whereby instead of attacking the appliance carrying adhesive of the proximal surface of the backing layer, the stomal output attacks the sacrificial material. In embodiments, the one or more substances advantageously includes a neutralizing substance as explained in more detail below. The neutralizing substance can be configured to effectively alleviate the damaging effects of the aggressive stomal output to the adhesive on the proximal surface of the backing layer, and to the skin surface of the user.

The releasable material is provided inter alia to protect the adhesive on the proximal surface of the backing layer, which provides the adhesive bond between the body side member and that part of the surface of the skin of a user that surrounds the stoma. This adhesive carries or keeps the ostomy appliance attached to the user's skin surface. Any stomal output proceeding along "side" surfaces of the stoma, i.e. between an innermost edge portion of the body side member around the stoma receiving opening and the stoma, tends to cumulate underneath the body side member, i.e. between the user's skin surface and the proximal surface of the body side member where the appliance carrying adhesive is located. Applying the body side member according to the present disclosure reduces or eliminates the cumulation of such stomal output underneath the body side member. Particularly, in embodiments wherein the releasable material comprises a neutralizer substance on the distal side of the backing layer, the stomal output can be neutralized before it can "creep under" the body side member and attack the skin and/or the adhesive.

When a stoma receiving opening of the body side member to the skin surface around the stoma is prepared, there will inevitably be a gap however small between the innermost edge portion of the body side member and the stoma's surface. A stoma needs room to work due to inter alia peristaltic movements of the intestine; it tends to enlarge when delivering stomal output and to shorten when not. On the skin surface, immediately adjacent to (including below, above, to the sides) this small gap, also referred to as the peristomal gap skin area, stomal output can enter and degrade the adhesive of the proximal surface of the backing layer as well as cause skin maceration. By providing a releasable material according to the disclosure, the releasable material can be released and be directed to the peristomal gap skin area.

In embodiments, the releasable material comprises a neutralizing substance and is configured to releasing a neutralizer substance, at least to the peristomal gap skin area at the central portion of the body side member. Some of the neutralizing substance may washout into the collecting bag because of the contact with the stomal output, but at least a portion of the neutralizing substance will flow into the peristomal gap skin area and interact with the stomal output to neutralize its harmful components. Moreover, inside a collecting bag, the relative humidity will quickly reach about 100%, so the presence of moisture is substantial. In embodiments where the releasable material is sensitive to moisture, the release of material may initiate shortly after applying the body side member, due to the high relative humidity in the collecting bag.

The output from the stoma may flow substantially continuously or it may enter the collecting bag in more or less strong and/or abrupt bursts, which can depend on the type of stoma. If the user is in an upright position, stomal output may flow continuously downward (in relation to the stoma) due to gravity and primarily wet (engage or contaminate) the centre portion of the body side member below the stoma. However, coming in abrupt bursts, and inside a collecting bag and with a distal wall of the collecting bag relatively close to, or even in contact with the stoma, the stomal output tends to be spread or smeared all over the centre portion of the body side member, also including the area of the body side member positioned above and to the sides of the stoma (seen in relation to the body side member as attached to the user's skin surface).

Often, the location of a stoma is on a lower part of the abdomen of the user. The exact location can cause difficulty and inconvenience for the user in terms of clothes or belts etc. getting "in the way" of the stoma and the ostomy appliance. In many situations, clothing of a user forces the distal wall of the collecting bag towards the stoma, whereby an abrupt burst of stomal output may for the duration of a relatively shorter or longer period fill a volume defined by the body side member, the distal wall of the collecting bag and any coupling means provided on the distal surface of the backing layer. Thus, in these situations, stomal output does not immediately become subjected to the force of gravity, but gathers in the defined volume, where it attacks also the area of the body side member above the stoma receiving openings.

According to the disclosure, stomal output, which often contains very aggressive bodily substances (e.g. including certain enzymes produced in the body), is prevented from reaching the polymeric matrix of the adhesive on the proximal surface of the device. This in turn helps to avoid both maceration damage to the skin surface (caused by the aggressive stomal fluids), and disintegration and/or failure of the adhesive on the proximal surface of the backing layer. This further provides a body side member having improved security against leakage occasioned by stomal output seeping under the adhesive, and thus presents with longer wear time (i.e. the time between substitutions of a used product for a fresh one). A longer product wear time may itself help provide less skin complications, since removal of the adhesive body side member of some appliances currently available from the skin surface, tends to strip skin cells of the epidermis. Thus, by providing a product offering a longer wear time, less product substitutions are required, resulting also in fewer occurrences of potential skin cell stripping. Additionally, there is an economic benefit to the user and/or to the health care system/insurance provider, when less substitutions and thus less products are required.

The body side member allows the releasable material to be released, particularly in response to contact with stomal output. The thereby released material is spread over the body side member and flows into the peristomal gap skin area. Thereby, an improved sealing effect is at least partly provided by an increase in the amount of material the aggressive stomal fluids must break down to reach and "attack" the adhesive on the body side member. As such, the releasable material provides a sacrificial component of the body side member, i.e. a material that is suitable for being "sacrificed" to avoid or slow the breaking down of the adhesive of the body side member.

In embodiments, each of the one or more overlays of releasable material and each of the individual cover layers are provided in an alternating configuration. Thus, in embodiments the structure of the body side member includes configurations wherein first an overlay of releasable material is provided on the distal surface, followed by an individual cover layer covering the first overlay of releasable material, and then followed by another overlay of releasable material and so forth. In embodiments, the alternating configuration of the overlays of releasable material and the individual cover layers is provided in (forms) a layered relationship. Thus, in these embodiments the alternating components, i.e. the overlays of releasable material and the individual cover layers, are provided alternately or interchangeably on the distal surface of the backing layer. First a layer formed by a first overlay of releasable material, then an individual cover layer, then again a layer formed by a second overlay of releasable material and then a next individual cover layer and so forth. In embodiments, multiple (a plurality of) overlays of releasable material are alternatingly superimposed with each of the individual cover layers to provide a laminate or laminate-type of construction.

In embodiments, the alternating configuration of the overlays of releasable material and the individual cover layers is provided in a contiguous (next to each other; having a common boundary or edge; touching) relationship. Thus, the alternating components are provided alternately or interchangeably on the distal surface of the backing layer. In embodiments, the components are alternately arranged in a side-by-side manner. In embodiments, the components are alternately arranged in a concentric manner around a common center. In embodiments, the components are alternately arranged in a parallel manner. In one example, a first overlay of releasable material is next to an individual cover layer, which in turn is next to a second overlay, which in turn is next to a second individual cover layer and so forth.

In embodiments, the alternating configuration of the overlays of releasable material and the individual cover layers is provided as combination of both a layered relationship and a contiguous relationship. This provides a both intuitive and stable configuration of the body side member.

Providing the components in such layered, contiguous or combined relationship offers an advantageous body side member inter alia in that the releasable material of each of the overlays of the releasable material can be released in one or more stages or "rounds of release." Each time an individual cover layer is removed from an overlay of releasable material, a "new" ("fresh" or "virgin") surface of releasable material will be exposed and become available for engagement with stomal output. Particularly, but not exclusively, the release of releasable material in such one or more stages is advantageous if the releasable material comprises a neutralizing substance. In that case, if a mass or volume of releasable material in a first overlay has been fully or substantially released (i.e. engaged with and/or "used by" stomal output), such that little or no more neutralizing substance is available within that particular first overlay, the adjacent individual cover layer can be removed to expose the "new" surface of releasable material to release the neutralizing substance into the stomal output. Moreover, the embodiments of the disclosure offer options of releasing a majority of the releasable material in a delayed or postponed manner, and/or to provide a sudden and/or massive release of sacrificial material, e.g. if a major and potentially leakage incurring event arises.

In embodiments, wherein the components are provided in a contiguous relationship, the releasable material can be provided as one or more annular segments surrounding the centre portion of the body side member. In embodiments, wherein two or more annular segments of releasable material are provided, the segments are further concentric in relation to each other. In embodiments, wherein the components are provided in a contiguous relationship, each overlay of releasable material can be provided such as to be covered on all surfaces thereof by an individual cover layer. In such embodiments, the releasable material can be seen to be contained within a volume or compartment formed by the individual cover layer. In other embodiments, each overlay of releasable material is provided such as to be covered by an individual cover layer only on one surface thereof, and/or only on one or two surfaces, each facing different individual cover layers. In embodiments, a plurality of overlays of releasable material covered by individual cover layers can be provided such as to form a pattern over at least a portion of the distal surface of the backing layer. In embodiments, the pattern is a regular pattern. In embodiments, the pattern is a random pattern. In embodiments, the body side member is configured such with the overlays of releasable material and the individual cover layers that a distalmost, and/or outermost component, is an individual cover layer. This is particularly advantageous if initial (i.e. very shortly after application of the body side member to the skin surface) release of the releasable material is not intended or not desired, thus offering further options for customizing release of releasable material. Thus, in embodiments, one of the individual cover layers forms a distalmost surface of the body side member.

In other embodiments, an overlay of releasable material is configured to form a distalmost surface of the body side member. This provides for a body side member wherein the release of the releasable material can begin as soon as the body side member is attached to the skin surface and engages the stomal output.

In embodiments, the body side member is configured to comprise different (individually distinct) types or kinds of releasable materials provided in different overlays. Thus, in embodiments, an overlay of releasable material being exposed first to stomal output can comprise a first species of releasable material and one or more other overlays of releasable materials can comprise one or more other (different) species of releasable material(s). In other embodiments, the releasable material in each overlay is identical. In other embodiments, one or more of the overlays comprises a composition of two or more different releasable materials.

In embodiments, one of the individual cover layers is configured to provide or define an entirety of the distal surface of the body side member. In other embodiments, the one individual cover layer is configured to extend over and cover only a portion of the distal surface. In one embodiment, the one individual cover layer is configured such that it only extends over a portion of a radial distance between the centre portion and/or the stoma receiving opening, and an outermost edge or outermost edge portion of the body side member. In other embodiments, two or more individual cover layers combine to form a portion or an entirety of the distal surface of the body side member.

In embodiments, one or both surfaces of an individual cover layer include an adhesive for attaching the cover layer to a respective overlay. In embodiments, the releasable material of each overlay is adhesive or includes an adhesive component for attaching the overlay to an individual cover layer. In embodiments, both the individual cover layer and the releasable material is adhesive or has adhesive properties or components.

In some implementations, the releasable material functions as a sacrificial material component of the body side member, i.e. a material that is suitable for being "sacrificed" to avoid or slow the breaking down of the adhesive on the proximal surface of the body side member when a respective overlay of releasable material is exposed to stomal output. This is advantageous in that the damaging effects of the aggressive stomal fluids on the primary adhesive, carrying the weight and creating the seal to the user's skin, of the ostomy appliance, are attenuated by sacrificing the releasable material. This in turn helps mitigating or at least prolonging the time needed for such stomal fluids to break down the adhesive on the proximal surface of the body side member. Thereby, an advantageous extension of the wear time of the ostomy appliance is achieved. Studies conducted by the inventors show that ensuring an unobstructed and efficient release of sacrificial material to engage with the aggressive stomal output, provide promising results in terms of significantly reducing the rate or speed of breakdown of the adhesive, allowing for increased wear time (life time) of the body side member. Moreover, the studies further suggest that for some implementations of the invention of the present disclosure, such efficient and unobstructed release is a factor having more weight than specifically controlling the direction of the releasable material to be sacrificed, such as directing it towards the stoma surface and/or an area of the body side member adjacent to the stoma, and/or to the stoma receiving opening of a body side member.

In addition, experience obtained by interviewing users shows that when an innermost edge portion of the body side member, or the centre portion of the body side member immediately adjacent to, or surrounding the stoma receiving opening, is engaged ("attacked") by aggressive stomal fluids, often results in a surprisingly (fast) break-down of the adhesive of the proximal surface of the body side member, which break-down begins at the innermost edge portion and egresses radially therefrom. This may in turn lead to failure of the appliance carrying adhesive, thus rendering the body side member and/or the whole ostomy appliance useless. Prior solutions have predominantly focussed on addressing such problems at the area of a body side member immediately adjacent to the stoma, i.e. they have tried to solve the issues at the innermost edge portion of the body side member.

Contrary to this, the present disclosure provides different and inventive solutions to overcome these and other problems. In some approaches, the problems are believed to be mitigated or reduced wholly or partly because of better options for controlling and/or distributing when and how much releasable material is exposed. By way of example, but not exclusively, this is achieved by distributing or "spreading" the releasable material over a larger or even all the distal surface of the body side member upon a cover layer being removed. In this regard, the inventors have found that, when the body side member is configured such that the releasable material enters onto a distalmost surface of the body side member, instead of being primarily directed towards the stoma's surface (the mucous membrane), and/or towards an area or location of the body side member immediately adjacent the stoma, the beneficial effects of the releasable material may be reached to the same or even to a better extent than by only directing the releasable material towards the stoma. In other words, removal of each individual cover layer (possibly in turn) allows for release of the releasable material predominantly over most of the distal surface of the body side member, instead of only releasing material in a radial direction towards the stoma, thereby achieving improved results.

In embodiments, release of the releasable material can be accelerated by providing finger pressure to a surface of the releasable material. The surface may or may not be at least partially covered by an individual cover layer. Additionally, or alternatively, the user does not provide finger pressure on the surface of the releasable material. Instead, the releasable material is released when the respective individual cover layer is removed because of the individual cover layer dissolving because of the exposure to the stomal output. These embodiments may help provide a simpler construction and still achieve the beneficial effects on sealing between the body side member and the skin and thus the increased wear time.

Thus, in embodiments, one or more of the individual cover layers comprise(s) a dissolvable material, such that, when the individual cover layer is subjected to water or a watery liquid, such as aggressive stomal fluids or mucus emanating or secreting from the mucous membrane of the stoma, the cover layer dissolves. In one embodiment, the dissolvable material comprises a polyolefin type polymer, such as polyvinyl alcohol (PVA).

In one embodiment, one or more of the individual cover layers comprises a thermoformable material. In one embodiment, one or more of the individual cover layers is formed of a thermoplastic polymer. In one embodiments, one or more of the individual cover layers comprises an elastic material. In one embodiment, one or more of the individual cover layers is additionally capable of transmitting moisture and may e.g. be made from polymers such as polyolefin types e.g. PE, PP or polybutylene, polyurethane, polyvinyl alcohol, ethylene vinyl acetate or other thermoplastic polysaccharides, polyether block amides such as PEBAX® from Arkema, France, block copolymers like styrene-isoprene-styrene block copolymers or ethylene acrylate block copolymers, polyesters such as polyethylene terephthalate (PET) or derivates thereof and any laminates made from such polymers. In embodiments, the cover layer comprises a thin foam layer made from e.g. polyurethane, polyethylene or polyvinyl acetate.

In embodiments, the releasable material can be shifted between at least a first and a second position in relation to its respective individual cover layer. In embodiments, one or more of the individual cover layers is/are configured to be plastically or elastically deformable, such as, but not limited to, by forming the cover layer from an anisotropic material.

In one embodiment, the releasable material of one or more of the overlays is configured to swell in response to absorption of moisture. In embodiments, the releasable material is configured to undergo a swelling action by absorption of moisture from the stomal output and/or from mucus emanating from the mucous membrane of the stoma. In embodiments, the releasable material includes a moisture absorbing component or substance. In embodiments, the moisture absorbing component has a high absorption capability or potential and in other embodiments, the moisture absorbing component has a small or low absorption capability. Suitable materials for the moisture absorbing component include, but are not limited to, superabsorbent polymers commonly made from poly-acrylic acid salts. In further embodiments, the adhesive of the proximal surface of the body side member is configured to undergo a swelling action by absorption of moisture and thus help create an improved seal between the stoma and the body side member and/or between the body side member and the skin surface. In embodiments, both the adhesive of the proximal surface of the backing layer and the releasable material is configured to undergo a swelling action by absorption of moisture.

In one embodiment, the releasable material is a viscoelastic material.

The proximal surface of the backing layer of the body side member comprises an adhesive. In embodiments, the adhesive comprises a plurality of different adhesive materials. In one embodiment, the different adhesive materials of the adhesive are provided in a side-by-side manner on the proximal surface of the backing layer. In one embodiment, the different adhesive materials of the adhesive are provided in a layered structure. In one embodiment, the different adhesive materials of the adhesive are provided primarily side-by-side, but with some overlapping portions of the different adhesive materials. Examples of suitable adhesive materials are given below.

In one embodiment, the body side member further comprises a reinforcing element. The reinforcing element may particularly, but not exclusively, include a sheet or layer of a polymeric film material, such as polyethylene (PE) or polypropylene (PP). Other film materials having additional characteristics, e.g. higher/lower liquid-, vapor- or gas-impermeability or odour control and others, may additionally and/or alternatively be used. Other reinforcing element options include mesh or mesh-shaped and/or woven materials. In one embodiment, the reinforcing element can be located between the adhesive on the proximal surface and the cover layer. In one embodiment, the reinforcing element can be embedded (contained completely) in the adhesive of the proximal surface of the body side member. In one embodiment, the reinforcing element includes reinforcing fibres.

One advantageous effect of the reinforcing element is that it helps provide a body side member which is more resistant to forces acting on it. Often a stoma is located on the lower portion of the abdomen of the user (corresponding to the location of the intestines). As described above, forces acting on the body side member include forces generated by the clothes of the user, such as at the waist lining of a pair of pants or jeans, and are often further amplified by the presence of a belt. The forces may be both pressure, pull and shear forces, and often in combination.

In one embodiment, one or more of the individual cover layers of the body side member comprises a sheet material. The sheet material may particularly, but not exclusively, include a sheet or layer of a polymeric film material, such as PE or PP. Other film materials having additional characteristics, e.g. odour control and others, may additionally and/or alternatively be used. In one embodiment, the sheet material layer is a dissolvable material, such as, but not limited to PVA. In embodiments, one or more of the individual cover layers comprises a coating. Thereby, in one exemplary process, a cover layer is formed to cover an overlay of releasable material by spraying a coating of a material of the cover layer onto an individual overlay during manufacture of the body side member.

In embodiments, each individual cover layer is formed by a resilient material. Suitable resilient materials for each individual cover layer include, but are not limited to, thermoplastic elastomers (TPE's) and/or mixtures thereof. In embodiments, cover layer is made by injection molding.

In embodiments, one or more of the individual cover layers comprises an erodible material. In such embodiments, an erosion rate of the erodible cover layer can be controlled, e.g. by controlling a thickness of the erodible respective cover layer. This is advantageous for achieving a body side member wherein the release of, or the engagement between, the stomal output and the releasable material of the body side member, can be delayed or postponed, and/or for controlling how and where the exposure of the adhesive of the proximal surface of the backing layer to the stomal output occurs.

In embodiments, one or more of the individual cover layers comprises a first and a second end or side, at least one of which is attached to one or more of the other components of the body side member. In one embodiment, a first end of an individual cover layer is attached to the backing layer of the body side member. In one embodiment, the first end of the cover layer is attached to a surface of the backing layer. In one embodiment, the first end of the cover layer is attached to the backing layer by embedding the first end in the material of the backing layer.

In embodiments, the releasable material comprises a fluid or a liquid. In embodiments, the releasable material is a pasta or paste. In embodiments, the releasable material is a gel or a substance or material suitable for gelling when exposed to certain conditions, such as exposed to moisture. In embodiments, a plurality of different materials of the releasable material are provided as a composition. In embodiments, the plurality of different materials of the releasable material is provided as a compound. In embodiments, the composition or compound comprises two or more substances.

In embodiments, the releasable material of each overlay comprises a matrix. In embodiments, the matrix of releasable material further comprises a neutralizing substance incorporated therein. In embodiments, the matrix of releasable material of each overlay is in the form of a gel, a foam, a film layer, paper or a coating, such as a solid coating or a powder coating. In embodiments, the matrix of releasable material and the neutralizing substance combine to form a colloidal solution, such as a sol. In embodiments, the releasable material or the matrix of the releasable material comprises one or more medicaments. In embodiments, the one or more medicaments is/are suitable for alleviating pain and/or problematic skin surface conditions of the peristomal skin surface.

In embodiments, each overlay of releasable material comprises different, individual materials. Thereby, the body side member can be configured such that a first overlay is configured to release one type of releasable material, and another overlay is configured to release a different type of releasable material. By providing different releasable materials in different individual overlays, a versatile product providing the user with many options for customizing the body side member according to individual requirements is achieved.

Pressure sensitive adhesives, particularly those containing hydrocolloids, is a particularly suitable group of adhesives being characterized by having a particulate phase of hydrocolloids dispersed in the adhesive phase or matrix. Adhesive containing hydrocolloids may absorb moisture from the skin to avoid occlusion of the skin, while maintaining its adhesive properties to skin. Moreover, an adhesive body containing hydrocolloids may have any thickness and still have the non-occlusive properties. A hydrocolloid adhesive may be processed as a hot melt and is easily moulded into specific shapes.

A typical pressure sensitive adhesive composition comprises a substantially homogeneous mixture of 10-60 weight percent of one or more rubbery elastomeric components, 5-60% of one or more absorbent particles, 0-50% tackifier resin, 0-10% of a plasticiser and 0-60% of a non-polar oily extender, based on the total weight of the composition. The rubbery elastomeric base could be selected from the group consisting of physically cross-linked elastomers (suitably block copolymers containing polystyrene blocks), a chemically cross-linked natural or synthetic rubbery elastomer, or a rubbery homopolymer. A physically cross-linked elastomer selected from block-copolymers of styrene, and one or more butadienes may be a styrene-butadiene-styrene block copolymer, a styrene-isoprene copolymer and is preferably a mixture of styrene-isoprene-styrene and styrene-isoprene block copolymers. A chemically cross-linked rubbery elastomer may be e.g. butyl rubber or natural rubber. A rubbery homopolymer may be a polymer of a lower alkene such as low density polyethylene or propylene, preferably atactic polypropylene or polyisobutylene. A tackifying resin optionally used in accordance with the invention is preferably a hydrogenated tackifier resin and is more preferred selected from a group comprising polymers and copolymers of cyclopentadiene, dicyclopentadiene, alpha-pinene or beta-pinene. When the physically cross-linked elastomer is a styrene-butadiene-styrene block copolymer or a styrene-isoprene-styrene block copolymer, the adhesive suitably comprises 0-10% of a plasticiser (e.g. CITROFOL® BII, Jungbunzlauer, Switzerland). The hydrocolloid particles preferably consist of one or more water-soluble or water swelling hydrocolloid polymers or gums. In other embodiments, the adhesive of the proximal surface of the body side member comprises one or more adhesives of the types disclosed in publications WO2007/082538 and WO2009/006901.

In embodiments, one or more overlays of releasable material is/are located radially closest to the centre portion of the body side member.

In embodiments, the adhesive of the proximal surface is provided on the backing layer, where the backing layer is provided distal to the adhesive of the proximal surface and proximal to each of the overlays of releasable material. In embodiments, the backing layer includes a film. In embodiments, the film includes a polyolefin material. In embodiments, the film material includes polyethylene. In embodiments, the backing layer carries the adhesive of the proximal surface of the body side member. In embodiments, each of the overlays of releasable material is provided on a distal surface of the backing layer. In embodiments, each of the overlays of the releasable material layer is attached to the distal surface of the backing layer by adhesion. These embodiments provide an advantageous simple construction of the body side member, which can be processed in a fast and reliable production process keeping manufacturing costs low while providing a new and versatile body side member for an ostomy appliance with several options for creating a customized and improved sealing to the skin surface.

In embodiments, each of the overlays of releasable material is configured to release the releasable material onto a substantial portion of the distal surface of the body side member. Thereby, a relatively large surface area of sacrificial material can be provided in little time (i.e. fast) for mitigating the damaging effects of the stomal output. Moreover, this provides a body side member offering many uses while having a relatively simple structure. For example, the disclosure provides an option for differentiating the amount of releasable material at any locality on the distal surface of the body side member. This is particularly advantageous in that more releasable material may be guided or directed to a location where it may be more needed than elsewhere on the distal surface of the body side member. Particularly, the releasable material can be guided both towards the stoma and away from it. Such implementations allow for multiple options for addressing the releasable material's beneficial effects to the right locations In one exemplary implementation and application of the body side member according to the present disclosure, a user initially customizes, such as by cutting, a stoma-receiving opening to an approximate size or circumference of the user's individual stoma. Next, the user can remove any protective liner(s) provided on the body side member, such as on the adhesive of the proximal surface of the backing layer and apply the body side member to the skin surface around the stoma.

From the above, it is understood that in conceiving the invention of the present disclosure, the inventors realized that releasable material does not per se have to be provided close to, or in direct contact with the stoma's surface, or on the peristomal skin surface, for the releasable material to provide its beneficial effects in protecting the adhesion between the skin surface and the body side member. Indeed, it was realized that the effect is achievable to a significant extent by releasing releasable material on the distal surface of the body side member, i.e. on the surface of the body side member facing away from the skin of the user, when the body side member is used. This is believed to be at least partly because of the provision of the releasable material as a sacrificial material and/or the creation of additional surface area of this sacrificial material by distributing it over a larger area of the body side member.

Even further, as an example, in embodiments wherein more than one kind of releasable material is provided in one or more overlays of the body side member, the helpful effect(s) presented by one releasable material may be amplified by the presence of another kind of releasable material to provide even better results in terms of reduction or elimination of leakage incidents.

In embodiments, the distal surface of the body side member comprises a first half of a coupling interface for coupling the body side member to a stomal output collecting bag. In one embodiment, the first coupling half is a flange adapted to provide a surface for attaching another coupling half in the form of an adhesive flange provided on a stomal output collecting bag. In embodiments, the first half of the coupling interface is configured as a flexible, planar annular flange optionally comprising an adhesive. The first coupling half is adapted to couple with a second coupling half provided around an inlet opening of a stomal output collecting bag by means of an adhesive. The adhesive coupling may provide a releasable or a permanent adhesive coupling engagement between the components.

In embodiments, the coupling half is an annular ring comprising an upstanding flange protruding from the distal surface perpendicular thereto for attaching another coupling half in the form of a coupling ring provided on a stomal output collecting bag. In one embodiment, a first coupling half is attached to the distal surface of the body side member. In embodiments, the first coupling half is attached to the distal surface by an adhesive or by welding, but other ways of attaching are acceptable. In embodiments, a first coupling half is attached to the distal surface of the body side member at a location radially closer to the stoma-receiving opening than where one or more openings are located.

In embodiments, the first coupling half is configured as an annular ring including an upstanding flange extending axially away from the distal surface of body side member. In one embodiment, the upstanding flange is configured to be perpendicular to the distal surface of the body side member. In embodiments, the distal surface of the backing layer further comprises an annular ring forming a first half of a coupling interface of the body side member, which is configured to couple with a second half of the coupling interface provided on a stomal output collecting bag.

In embodiments, the stomal output collecting bag includes a front wall forming a distal side and a rear wall forming a proximal side. Each wall can be made of gas- and liquid impermeable foil-material (for example of polyethylene (PE), polyvinyl-chloride (PVC) or ethylene-vinyl-acetate (EVA)) that is welded around the edges or the rim, to form a bag defining a waste collection chamber. The bag may be welded only partly around the rim so that a discharge opening for emptying the bag is provided at the bottom of the bag. In that case, the bag may be provided with means for closing that opening. An inlet opening is provided in the rear wall and placed in the upper part of the collecting bag, so that when a user stands up, the inlet opening will locate above a midline of the collecting bag. This provides a major collecting volume portion below the inlet opening of the bag. Thus, a top of the collecting bag is defined as the portion of the bag nearest to the inlet opening, and the bottom is defined as an opposite portion of the bag.

In embodiments, each of the overlays of the releasable material comprises an adhesive. In other embodiments, each of the overlays of the releasable material comprises a powder. In other embodiments, each of the overlays of the releasable material comprises a liquid. In other embodiments, each of the overlays of the releasable material comprises a gel. In other embodiments, each of the overlays of the releasable material comprises a paste or pasta. In other embodiments, each of the overlays of the releasable material comprises a plurality of dissolvable pellets. In yet other embodiments, the releasable material comprises a combination of any one or more of an adhesive, a powder, a liquid, a gel, a paste and/or a plurality of pellets. In embodiments, the releasable material may be provided from manufacture in one of the forms mentioned here and be configured to transition into one or more of the other forms. As one example, a paste that may start to gel and/or become a gel in response to uptake of moisture. These options each provides one or more different advantages including, but not limited to, manipulability, shelf life, suitability for different kinds of stomal output, processing characteristics and others. By selectively applying these options, individually or in combination, to meet particular requirements of a target ostomy type, the suitability of the appliance and the improvement in sealing effect reducing or eliminating the risk of leakage, can be significantly enhanced.

Particularly, in embodiments wherein the releasable material comprises an adhesive, suitable materials include adhesives, such as, but not limited to, adhesive pastes. Suitable materials for a paste-type adhesive comprise adhesives of the types disclosed in WO2010/069334. Other types of adhesive pastes are also acceptable.

In another aspect of the disclosure, use of the body side member 20 for an ostomy appliance as disclosed herein for reducing the frequency of stomal output leakage incidents in further contemplated. The advantageous effects provided by the embodiments of the body side member 20, aid in alleviating the nuisances of output leakages often encountered by users of ostomy appliances. This is at least partly achieved by the externalization of the releasable material providing a better security against disintegration of the skin adhesive on the proximal surface of the backing film of the body side member. Use of the body side member according to the present disclosure allows for an increased wear time of an ostomy appliance.

The Neutralizing Substance

By neutralizing substance is herein meant a substance capable of neutralizing or at least minimizing the level of skin- or adhesive-aggressiveness of the output. In embodiments, the neutralizer comprises a clay, such as organophilic clay, for example bentonite or synthetic clay such as laponite. In embodiments, the neutralizing substance may be potato-derived inhibitors or protease inhibitors. Examples of potato-derived inhibitors such as potato protein is disclosed in EP 1 736 136.

In embodiments, the releasable material is in the form of a matrix composition with a neutralizing substance incorporated. The neutralizing substance may be dissolved in the matrix composition or it may be dispersed as particles in the matrix. In embodiments, the matrix may be in the form of coated neutralizing substance particles.

In embodiments, the matrix is designed to release neutralizing substance to the environment when the matrix is exposed to certain conditions. Such conditions may for example be in the presence of output from the stoma or in the presence of moisture as such.

In embodiments, the matrix is in the form of a gel, foam, film layer or paper or a coating.

In embodiments, a suitable example of a matrix composition could be an adhesive comprising 50% w/w polyisobutylene (PIB) and 25% w/w CMC and 25% w/w pectin.

In embodiments, a matrix composition in the form of a water-soluble film could be a PVOH based thermoplastic film, such as a Monosol® 7031 film from kurakay WS Film Division™, Portage, Ind., United States.

In embodiments, the matrix is soluble in water or a component of the output. It may be slowly soluble, by slowly is herein meant that the matrix layer will not be washed away instantly, but will slowly dissolve during wear time of the wafer.

In embodiments, the matrix can absorb moisture and turn into a gel like material when wetted. The gel may be delivered in dry form but swell into a gel when brought into contact with moisture. The gel may be slowly soluble in water or in a component of the output or it may be insoluble but able to release the neutralizing substance when exposed to the output or moisture.

In embodiments, the matrix comprises polysaccharides and/or hydrocolloids. The polysaccharides or hydrocolloids may dissolve or hydrate when exposed to output, thereby releasing neutralizing substance.

In embodiments, the matrix comprises protein. In embodiments, the matrix comprises gelatine.

In embodiments, the matrix is a material capable of forming a gel when wetted. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine. In embodiments, the matrix is substantially non-adhesive. By non-adhesive is meant that it is not adhesive, though it may under certain circumstances become slightly sticky.

In another aspect, the disclosure relates to an ostomy appliance including a body side member as described herein and a stomal output collecting bag configured to be attached to the distal surface of the body side member.

In one embodiment, the ostomy appliance is a one-piece ostomy appliance, i.e. without a coupling interface between the body side member and the stomal output collecting bag. In another embodiment, the ostomy appliance is a two-piece appliance including a coupling interface for connecting a stomal output collecting bag to the body side member by connecting or coupling first and second coupling halves to each other.

In one embodiment, the stomal output collecting bag comprises a second half of a coupling interface that is configured to couple with a first half of the coupling interface on the body side member to attach the stomal collecting bag to the body side member.

In one embodiment, at least the distal surface of the body side member formed by the cover layer is defined by a first zone and a second zone surrounding the first zone, the first zone being radially inside of an annular connection between a first half of a coupling interface and the body side member, and the second zone being radially outside of the annular connection between the first half of the coupling interface and the body side member.

DETAILED DESCRIPTION OF THE DRAWINGS

Figure 1:
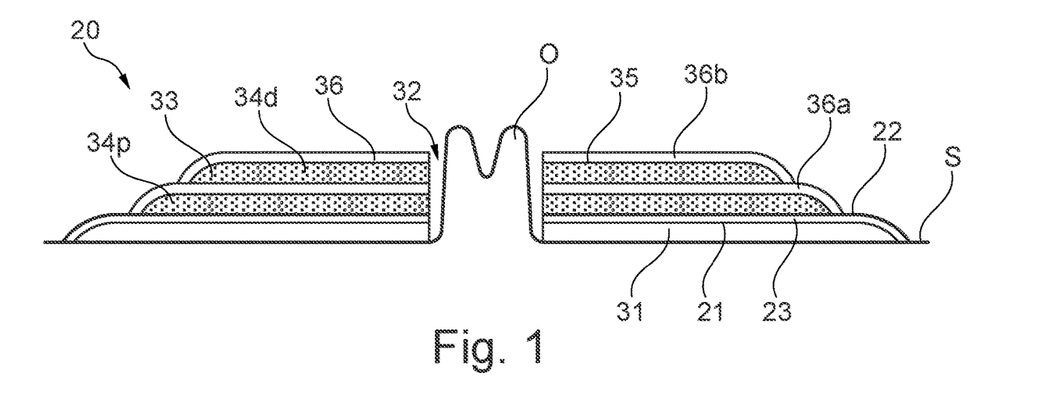
FIG. 1 is a schematic, cross-sectional view of one embodiment of a body side member of an ostomy appliance comprising a releasable material.

FIG. 1 is a cross-sectional view of one embodiment of a body side member 20 of an ostomy appliance according to the present disclosure. The body side member 20 includes a backing layer 23 comprising a proximal surface 21 and a distal surface 22. At least a portion of the proximal surface 24 of the backing layer 23 comprises an adhesive 31 (forming the "underside" in FIG. 1). In the FIG. 1 embodiment, the body side member 20 includes two overlays 34p, 34d of a releasable material 33, which are provided in a layered relationship. The proximal-most overlay 34p is provided on the distal surface 22 of the backing layer 23. Each of the proximal-most overlay 34p and the distal-most overlay 34d are shown in FIG. 1 to be covered by individual cover layers 36. Each of the individual cover layers 36 is configured to be individually removable from off the respective overlays 34d, 34p to expose a surface 35 of the respective overlay of releasable material 34d, 34p. FIG. 1 further shows a stoma O of the user extending through a stoma receiving opening 32 of the body side member 20. The stoma receiving opening 32 may be provided during manufacture of the body side member 20, or it may be provided by the user in preparing the body side member 20 for attachment to the skin surface around the stoma O. In the FIG. 1 embodiment, the proximal-most overlay 34p comprising releasable material 33 is provided proximal to individual cover layer 36a. The distal-most overlay 34d comprising releasable material 33 is provided proximal to individual cover layer 36b, and distal to individual cover layer 36a. FIG. 1 illustrates a situation immediately after the body side member 20 has been attached to the skin surface S around the stoma O of a user.

If, or when cover layer 36b is removed, releasable material 33 from the distal-most overlay 34d can be released and engage with stomal output. This is illustrated in FIG. 2, which shows some of the releasable material 33 released and engages with stomal output U on a the distal-most surface of the body side member 20, seen in relation to the skin surface S.

Figure 2:
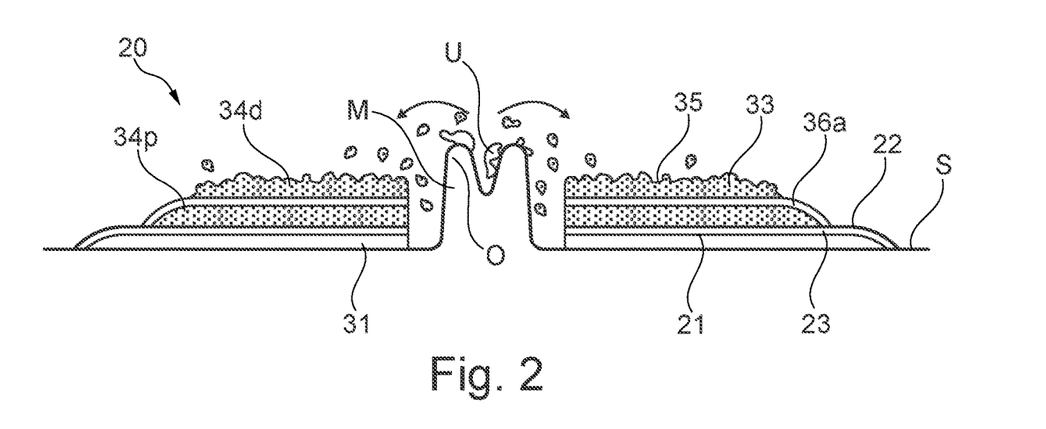
FIG. 2 is a schematic cross-sectional view of one embodiment showing a body side member comprising a releasable material.

FIG. 2, which is a cross-sectional view of one embodiment of the body side member 20 further illustrates how some of the releasable material 33 has begun to engage with stomal output U, illustrated by way of example at different positions in FIG. 2. In addition to engaging with the stomal output U, the releasable material also engages with moisture (or mucin) emanating from the mucous membrane M of the stoma O, and in some situations also with moisture (sweat) emerging from the skin surface S of the user. The mass of releasable material 33 of each of the overlays 34$d$, 34$p$ acts as a material being "sacrificed" to the aggressive stomal output U, every time an individual cover layer 36$a$, 36$b$ is removed. In some implementations, the releasable material 33 comprises one or more neutralizing substances which release or engage with the stomal output U, and thereby neutralizes the damaging contents of the stomal output such that the aggressive elements thereof do not break down the adhesive 31 of the proximal surface 21 of the backing layer 23. In the embodiments shown in FIGS. 1 and 2, releasable material 33 can additionally engage with the stoma's surface at the side thereof, indicated by arrows R, and thereby help to improve the seal between the body side member 20 and the skin surface S, and/or slow or eliminate the possibility of the stomal output U of reaching the adhesive 31. However, the body side member 20 is not necessarily required to abut or be very close to the stoma's surface, as shown in FIGS. 1 and 2. In any event, the major portion of the releasable material 33 comes into engagement with the stomal output U by removal of an individual cover layer 36$a$, 36$b$. The exposed releasable material 33 can configure, e.g. by taking up moisture and/or blending with the stomal output, to cumulate (or gather) on the distal-most surface of the body side member 20, seen in relation to the skin surface S. This may additionally help protect the remainder of the releasable material 33 underneath the cumulated material from breaking down rapidly and further to help provide a prolonged availability of releasable material 33 for use as sacrificial material.

Figure 3:
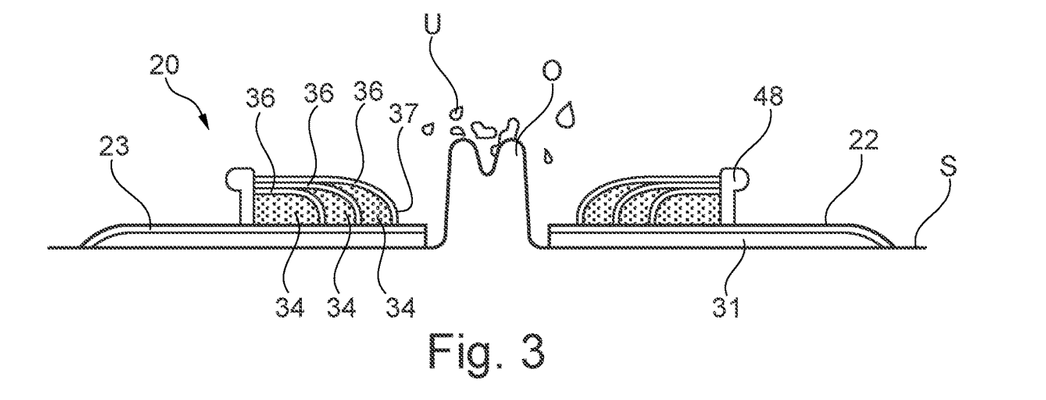
FIG. 3 is a schematic cross-sectional view of a portion of one embodiment illustrating one embodiment the body side member.

FIG. 3 is a schematic cross-sectional view illustrating a portion of one embodiment of the body side member 20 wherein the overlays 34 and the individual cover layers 36 are provided in an alternating configuration. Additionally, the overlays 34 and the individual cover layers 36 are provided in a contiguous relationship, where they are shown next to each other in a repeating sequence. An innermost edge portion 37 of the body side member 20 is shown to be near the stoma O. At least a portion of the innermost edge portion 37 is provided by an overlay 34 of releasable material, which is shown in FIG. 3 to be exposed to stomal output U. At a distalmost portion of each cover layer 36, the cover layer 36 engages with a neighbouring cover layer 36. Each overlay of releasable material 33 can be exposed "one at a time", thereby providing a body side member 20 with the option of releasing the releasable material 33 in stages.

Figure 4:
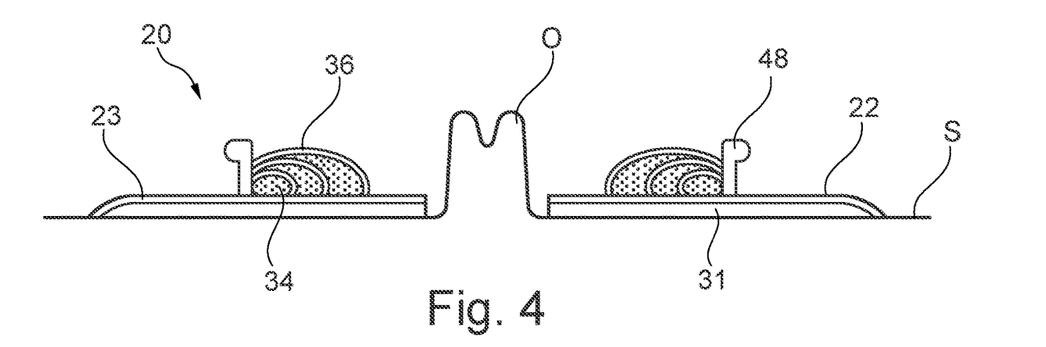
FIG. 4 is a schematic cross-sectional view of a portion of one embodiment illustrating one embodiment of the body side member.

FIG. 4 is a schematic cross-sectional view illustrating a portion of one embodiment of the body side member 20. Each of the individual cover layers 36 confines an overlay 34 of releasable material 33. Each confined overlay 34 and respective individual cover layer 36 in turn confines another overlay 34 and its respective individual cover layer 36. Each overlay of releasable material 33 can be exposed "one at a time", thereby providing a body side member 20 with the option of releasing the releasable material 33 in stages.

Figure 5:
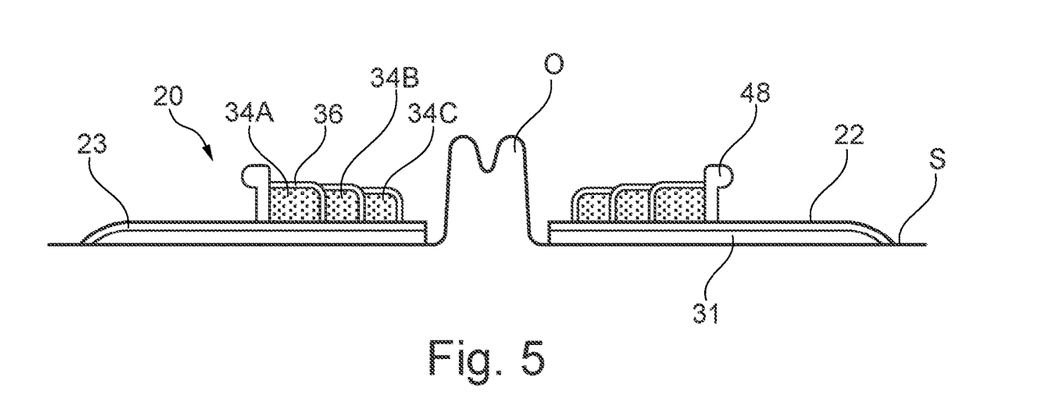
FIG. 5 is a schematic cross-sectional view of a portion of one embodiment of the body side member.

FIG. 5 is a schematic cross-sectional view of a portion of one embodiment of a body side member 20—Each of the individual cover layers 36 confines an overlay 34 A,B,C of releasable material 33. Each individual cover layer 36 covers at least a portion of the surface area of each overlay 34 A,B,C. Another portion of the surface area of a respective overlay 34 A,B,C is covered by an adjacent or neighbouring individual cover layer 36. Thereby, each overlay of releasable material 33 can be exposed "one at a time", thereby providing a body side member 20 with the option of releasing the releasable material 33 in stages.

Figure 6:
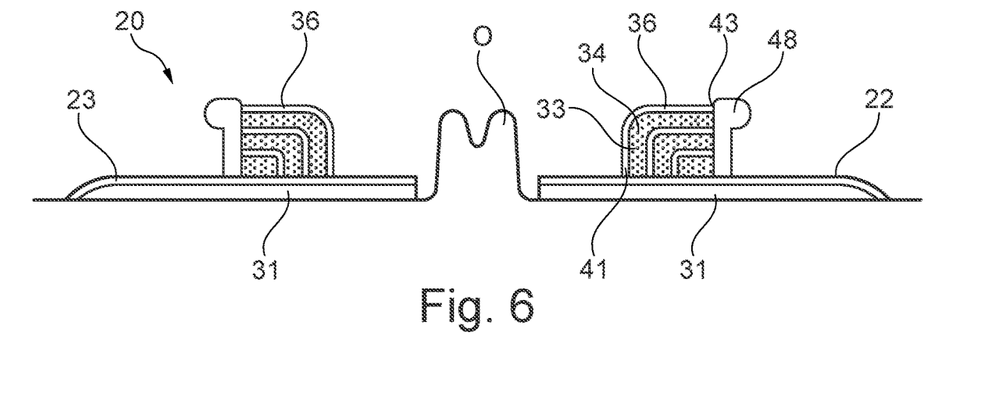
FIG. 6 is a schematic cross-sectional view of a portion of one embodiment of the body side member.

FIG. 6 is a schematic cross-sectional view of a portion of one embodiment of a body side member 20. A plurality of individual cover layers 36 each covers an overlay 34 of releasable material 33. In the embodiment of the body side member 20 illustrated in FIG. 6, three individual cover layers 36 and respective overlays 34 are provided. A first end 41 of each of the individual cover layers 36 is shown attached to the distal surface 22 of the backing layer 23. A second end 43 of each of the individual cover layers 36 engages a radially innermost surface of an upstanding flange of a first half 48 of a coupling interface for attaching the body side member 20 to a second half of the coupling interface provided on a stomal output collecting bag (not shown). Releasable material 33 can be exposed from each overlay 34 in turn when an individual cover layer 36 is removed. The view of FIG. 6 illustrates one example of embodiments wherein the relationship between the overlays of releasable material 34 and the individual cover layers 36 is a combination of a layered and a contiguous relationship.

Figure 7:
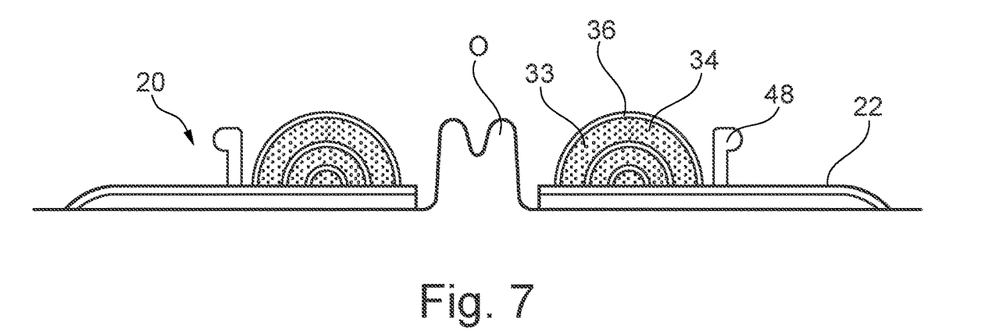
FIG. 7 is a schematic cross-sectional view of a portion of one embodiment of the body side member.

FIG. 7 is a schematic cross-sectional view illustrating a portion of one embodiment of the body side member 20, wherein the releasable material 33 of overlay 34$a$ is different from the releasable material 33 of overlay 34$b$, in turn different again from the releasable material of overlay 34$c$.

Figure 8:
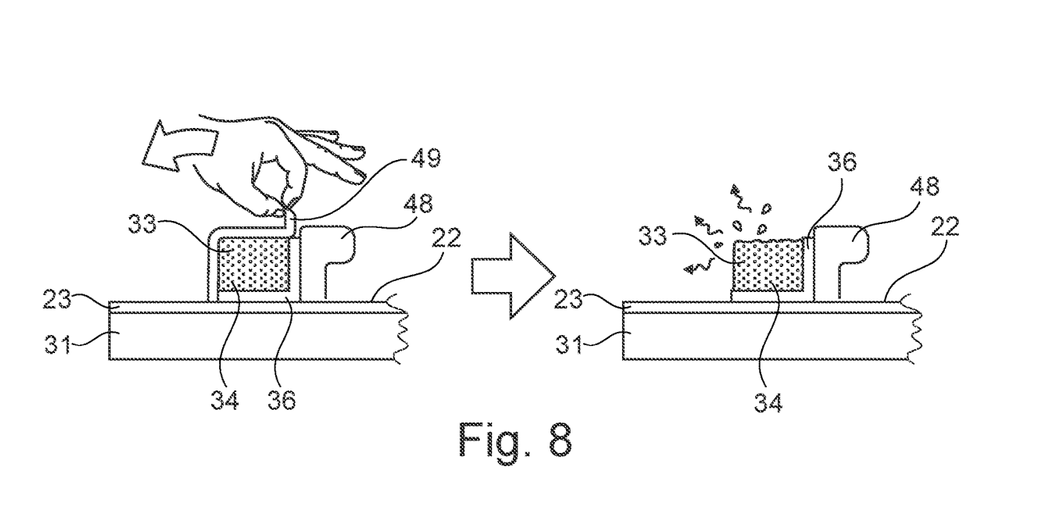
FIG. 8 is a schematic cross-sectional view of a portion of one embodiment of the body side member.

FIG. 8 is a schematic cross-sectional view of a portion of one embodiment of the body side member 20 in a first situation, wherein an overlay 34 is covered by an individual cover layer 36 and configured to initially completely confine the releasable material 33 of the overlay 34. FIG. 8 further shows a second situation, wherein at least a portion of the cover layer 36 has been removed by a user, using his/her fingers to detach the portion of the cover layer 36 and thereby make the releasable material 33 of the overlay 34 exposed to stomal output. Suitably, the cover layer 36 is shown to comprise a tab 49 or similar allowing for easy gripping and removal of the cover layer 36, or at least a portion thereof as shown. Although FIG. 8 simply illustrates one overlay 34, more than one overlay 34 with each an individual cover layer 36 can be provided.

Figure 9:
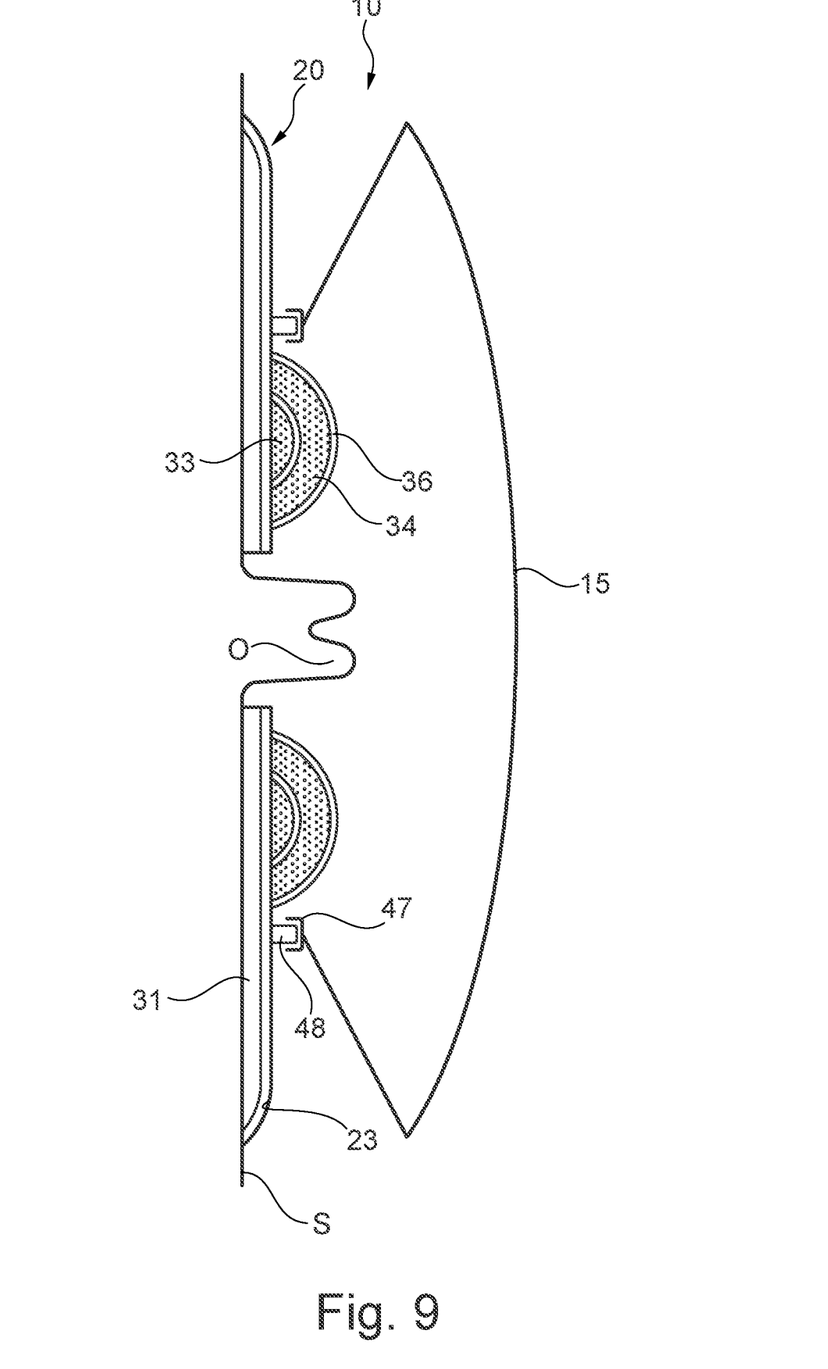
FIG. 9 is a schematic, cross-sectional view of one embodiment of an ostomy appliance comprising a body side member according to the present disclosure attached to the skin surface of a user.

FIG. 9 is a schematic cross-sectional view of one embodiment of a body side member 20 of an ostomy appliance 10 in use, i.e. attached to the skin surface S around the stoma O of a user. The body side member 20 is shown with two overlays 34 of releasable material 33, each covered by an individual cover layer 36. In the FIG. 9 embodiment, each of the individual cover layers 36 comprises a dissolvable material, such that it dissolves and is removed when subjected to stomal output. In response to the individual cover layer 36 being removed, the releasable material 33 of a respective overlay 34 is exposed and can engage with the stomal output as explained in this disclosure. The ostomy appliance shown in the FIG. 9 embodiment is of the two-piece type, comprising a coupling interface including first and second halves 47, 48 for attaching the body side member 20 and the collecting bag 15 to each other. Thus, alternatively, or additionally, the distal-most cover layer 36 could also be completely removed manually by the user before coupling the collecting bag 15 to the body side member 20. Thereby, release of releasable material can begin as soon as the ostomy appliance 10 is attached to the skin surface S of the user. This can be particularly advantageous for users (e.g. ileostomists) having a very liquidly output type.

In the embodiment of FIG. 9, the first coupling half 48 is an annular ring comprising an upstanding flange protruding from and perpendicular to the distal surface 22 of the backing layer 23. The flange is configured for attaching the second coupling half 47 in the form of a coupling ring provided on the stomal output collecting bag 15. In embodiments, the first coupling half 48 is attached to the distal surface 22 by an adhesive or by welding, but other ways of attaching are acceptable.

FIG. 9 illustrates one embodiment of an ostomy appliance 10 including a body side member 20 as described herein and a stomal output collecting bag 15 configured to attached to the distal surface 22 of the backing layer 23. As illustrated in FIG. 9, the ostomy appliance 10 is a two-piece appliance including a coupling interface comprising a first half 48 and a second half 47 for connecting a stomal output collecting bag 15 to the body side member 20. It is to be understood that the ostomy appliance 10 may also be a one-piece ostomy appliance, i.e. without a coupling interface between the body side member 20 and the stomal output collecting bag 15.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A body side member adapted to secure a waste collecting bag of an ostomy appliance to a user, comprising:
   a backing layer comprising a proximal surface and a distal surface, at least a portion of the proximal surface comprising an adhesive adapted to adhere the body side member to skin of a user;
   one or more overlays of a releasable material disposed on a portion of the distal surface of the backing layer; and
   a stoma receiving opening extending through the body side member;
   wherein a distal surface of each of the one or more overlays of the releasable material is covered by an individual cover layer,
   wherein, during use when the individual cover layer removed from the distal surface of the one or more overlays of the releasable material an exposed portion of the distal surface of the one or more overlays of the releasable material is exposed inside of the waste collecting bag for engagement with stomal output from the user.

2. The body side member of claim 1, wherein the one or more overlays of the releasable material comprises:
   a first overlay of releasable material disposed on the distal surface of the backing layer;
   a first individual cover layer disposed on the distal surface of the first overlay of releasable material; and
   a second overlay of releasable material disposed on the first individual cover layer.

3. The body side member of claim 2, wherein the second overlay of releasable material forms a distalmost surface of the body side member.

4. The body side member of claim 2, wherein a second individual cover layer is disposed on a distal surface of the second overlay of releasable material, and the second individual cover layer forms a distalmost surface of the body side member.

5. The body side member of claim 1, wherein the individual cover layer comprises a sheet material.

6. The body side member of claim 1, wherein the individual cover layer comprises a coating applied to the distal surface of each of the one or more overlays of the releasable material.

7. The body side member of claim 1, wherein the individual cover layer comprises a thermoformable material.

8. The body side member of claim 1, wherein the individual covers layer comprises a dissolvable material that dissolves in response to exposure to the stomal output.

9. The body side member of claim 1, wherein the one or more overlays of the releasable material comprises a laminate of three overlays of releasable material disposed on the distal surface of the backing layer, with a first individual cover layer disposed on a distal surface of a first of the three overlays of the releasable material, a second individual cover layer disposed on a distal surface of a second of the three overlays of the releasable material, and a third individual cover layer disposed on a distal surface of a third of the three overlays of the releasable material.

10. The body side member of claim 1, wherein the distal surface of the backing layer further comprises an annular ring forming a first half of a coupling interface of the body side member that is configured to couple with a second half of the coupling interface provided on the waste collecting bag.

11. The body side member of claim 1, wherein the one or more overlays of the releasable material comprises at least one of an adhesive, a powder, a paste, a liquid, a gel, a plurality of pellets, or any combination thereof.

12. The body side member of claim 1, wherein the one or more overlays of the releasable material is configured to swell in response to absorption of moisture.

13. The body side member of claim 1, wherein the one or more overlays of the releasable material comprises a neutralizer that is adapted to neutralize the stomal output from the user.

14. The body side member of claim 1, wherein the waste collecting bag is attachable to the body side member outside of an outer perimeter of the one or more overlays of the releasable material disposed on the distal surface of the backing layer.

15. The body side member of claim 13, wherein the neutralizer comprises an organophilic clay.

16. The body side member of claim 13, wherein the neutralizer comprises a synthetic clay.

17. The body side member of claim 13, wherein the neutralizer comprises a potato-derived inhibitor.

18. The body side member of claim 13, wherein the neutralizer comprises a protease inhibitor.

19. The body side member of claim 1, wherein the one or more overlays of the releasable material comprises a matrix comprising a polysaccharide that is adapted to dissolve when exposed to the stomal output from the user and release a neutralzier to neutralize the stomal output from the user.

20. The body side member of claim 1, wherein the one or more overlays of the releasable material comprises a matrix comprising a hydrocolloid that is adapted to hydrate when exposed to the stomal output from the user and release a neutralzier to neutralize the stomal output from the user.

21. The body side member of claim 1, wherein the one or more overlays of the releasable material comprises a neutralizer, and when the individual cover layer is removed from the distal surface of the one or more overlays, the neutralizer is released from the exposed portion of the distal surface of the one or more overlays and spreads into a peristomal gap formed between the body side member and the stoma.

* * * * *